(12) United States Patent
Heuser

(10) Patent No.: US 6,364,900 B1
(45) Date of Patent: Apr. 2, 2002

(54) EMBOLISM PREVENTION DEVICE

(76) Inventor: Richard R. Heuser, 2626 E. Arizona Biltmore Cir., No. 9, Phoenix, AZ (US) 85016

(*) Notice: Subject to any disclaimer, the term of this patent is extended or adjusted under 35 U.S.C. 154(b) by 0 days.

(21) Appl. No.: 09/353,104

(22) Filed: Jul. 14, 1999

(51) Int. Cl.$^7$ ............................ A61F 2/06; A61M 29/00
(52) U.S. Cl. ..................................... 623/1.11; 606/194
(58) Field of Search ...................... 606/200, 195, 606/127, 108, 191, 192, 194, 198; 604/52, 53; 128/344; 623/1.11

(56) References Cited

U.S. PATENT DOCUMENTS

| | | | |
|---|---|---|---|
| 4,445,892 A | | 5/1984 | Hussein et al. |
| 4,771,777 A | * | 9/1988 | Horzewski et al. ......... 128/344 |
| 4,911,163 A | * | 3/1990 | Fina ............................ 606/127 |
| 4,994,071 A | | 2/1991 | MacGregor |
| 5,199,939 A | | 4/1993 | Dake et al. |
| 5,256,141 A | * | 10/1993 | Gencheff et al. ............. 604/53 |
| 5,261,878 A | * | 11/1993 | Galindo ......................... 604/96 |
| 5,620,457 A | * | 4/1997 | Pinchasik et al. .......... 606/194 |
| 5,628,786 A | * | 5/1997 | Banas et al. ............... 623/1.11 |
| 5,632,760 A | * | 5/1997 | Sheiban et al. ............. 606/191 |
| 5,632,762 A | * | 5/1997 | Myler ......................... 606/194 |
| 5,645,560 A | * | 7/1997 | Crocker et al. ............. 606/192 |
| 5,695,498 A | * | 12/1997 | Tower ......................... 606/108 |
| 5,735,892 A | * | 4/1998 | Myers et al. ............... 606/198 |
| 5,833,644 A | * | 11/1998 | Zadno-Azizi et al. ......... 604/52 |
| 5,833,650 A | * | 11/1998 | Imran .......................... 604/53 |
| 5,893,867 A | | 4/1999 | Bagaoisan et al. |
| 5,899,917 A | * | 5/1999 | Edwards et al. ............ 606/195 |
| 5,980,532 A | * | 11/1999 | Wang .......................... 606/108 |
| 6,013,085 A | * | 1/2000 | Howard ...................... 606/108 |
| 6,022,336 A | * | 2/2000 | Zadno-Azizi et al. ....... 606/194 |

OTHER PUBLICATIONS

*Catherization and Cardiovascular Interventions* 47:243–250 (1999) "An Embolization Containment Device" by Oesterle et al.

* cited by examiner

Primary Examiner—Eduardo C. Robert
(74) Attorney, Agent, or Firm—Kolisch, Hartwell, Dickinson, McCormack & Heuser

(57) ABSTRACT

An apparatus for preventing embolisms resulting from an operation being performed in a body conduit by an instrument. The apparatus includes a selectively actuable conduit blocking mechanism that is actuated prior to performing the operation to thereby block the conduit while the operation is being performed upon an interior wall of the conduit, wherein the conduit blocking mechanism is de-actuated subsequent to the operation being performed. A transporting mechanism is movable within the conduit. The conduit blocking mechanism and the instrument are disposed at separate positions upon the transporting mechanism. The apparatus may be used for stent delivery, vessel predilation, or other operations.

16 Claims, 6 Drawing Sheets

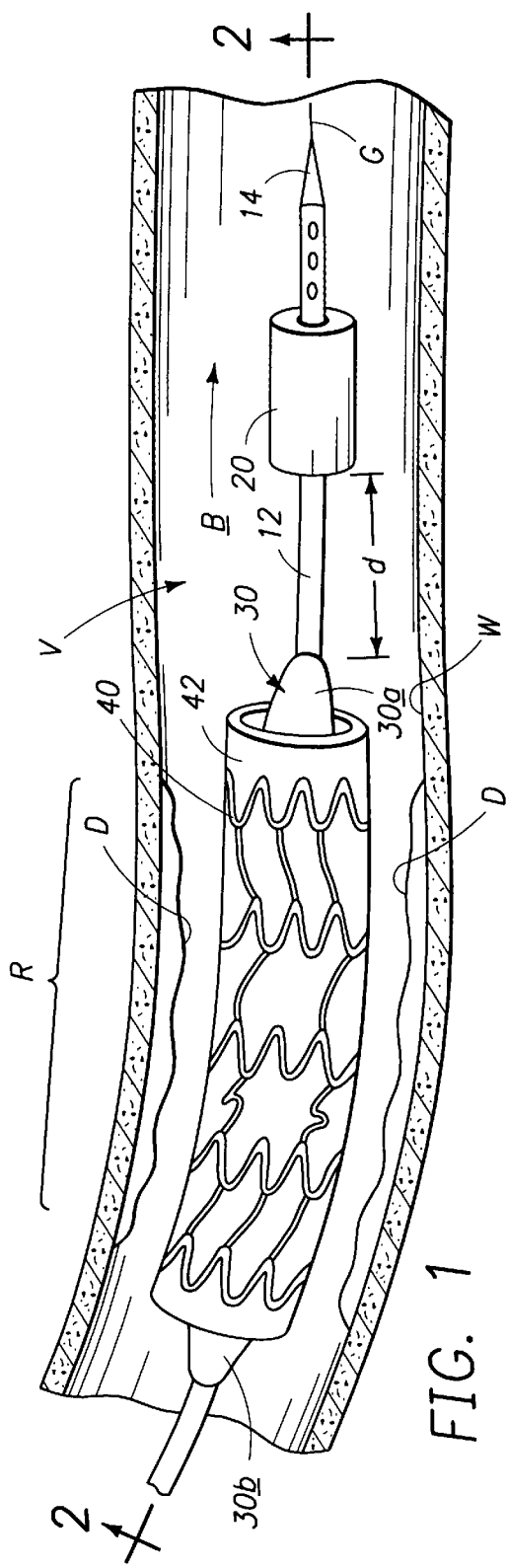
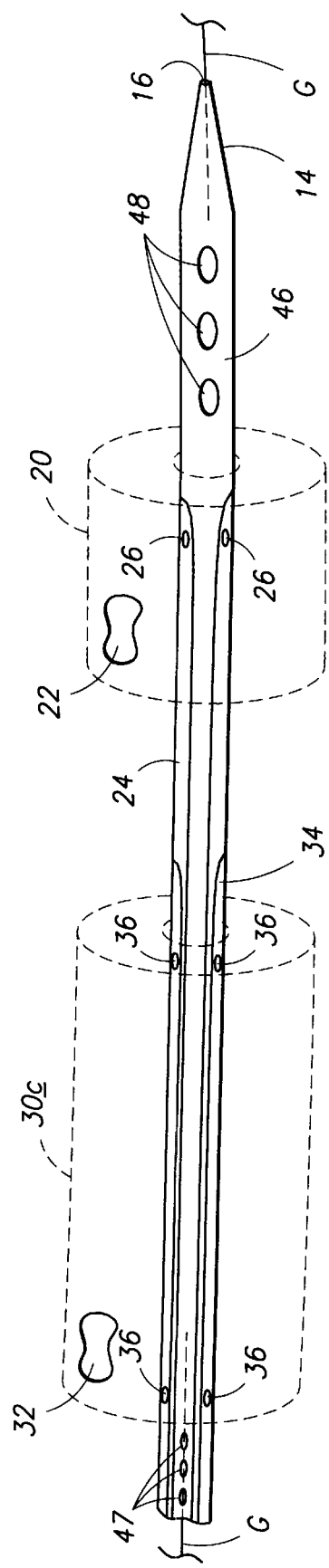
FIG. 1
FIG. 2

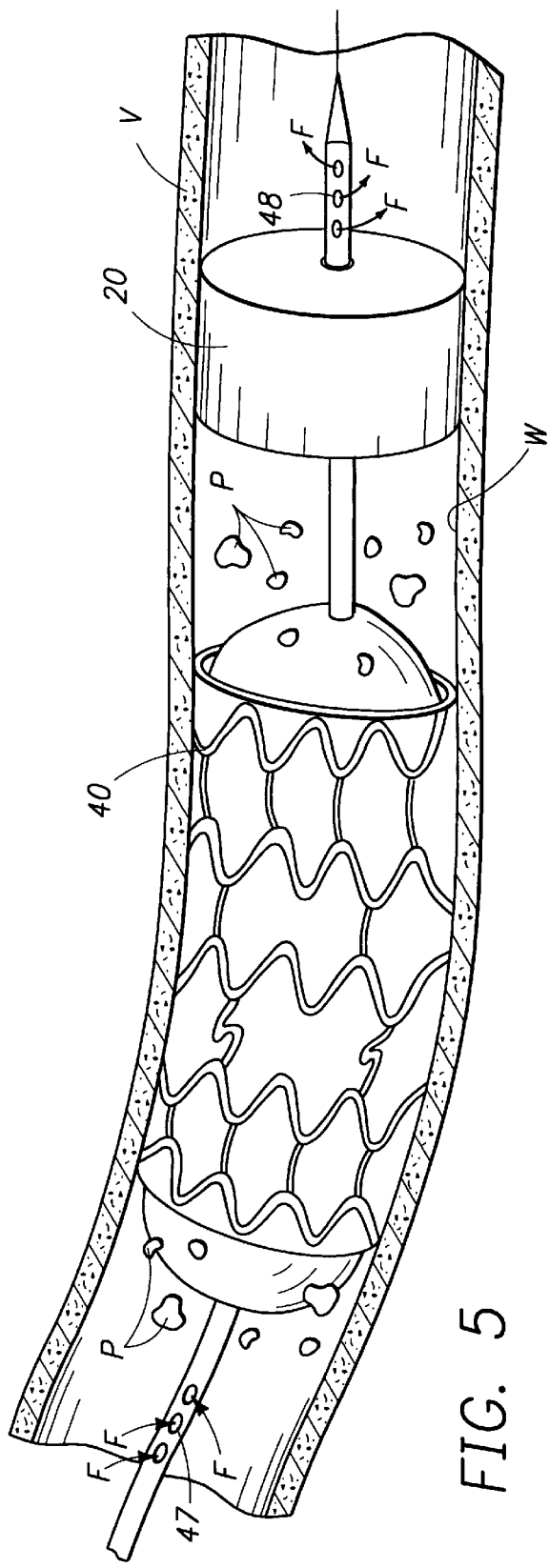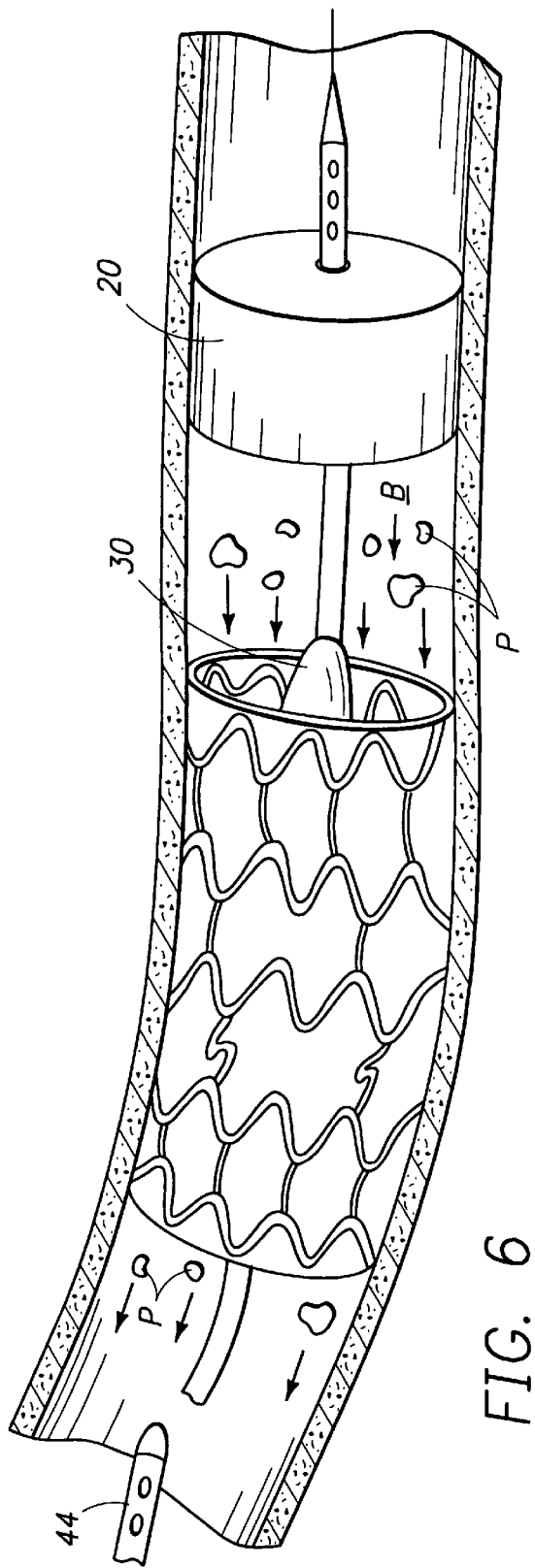

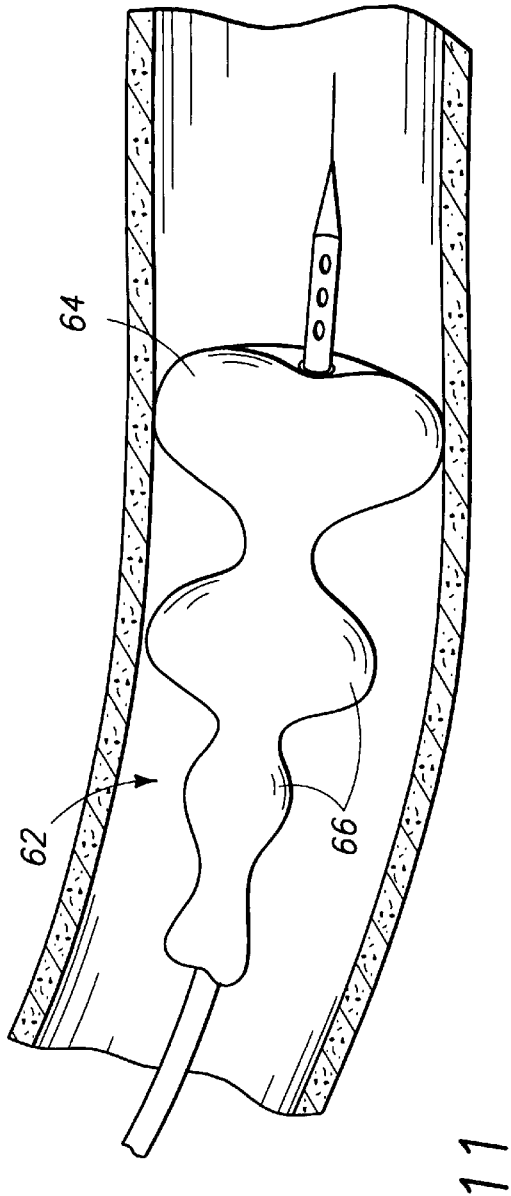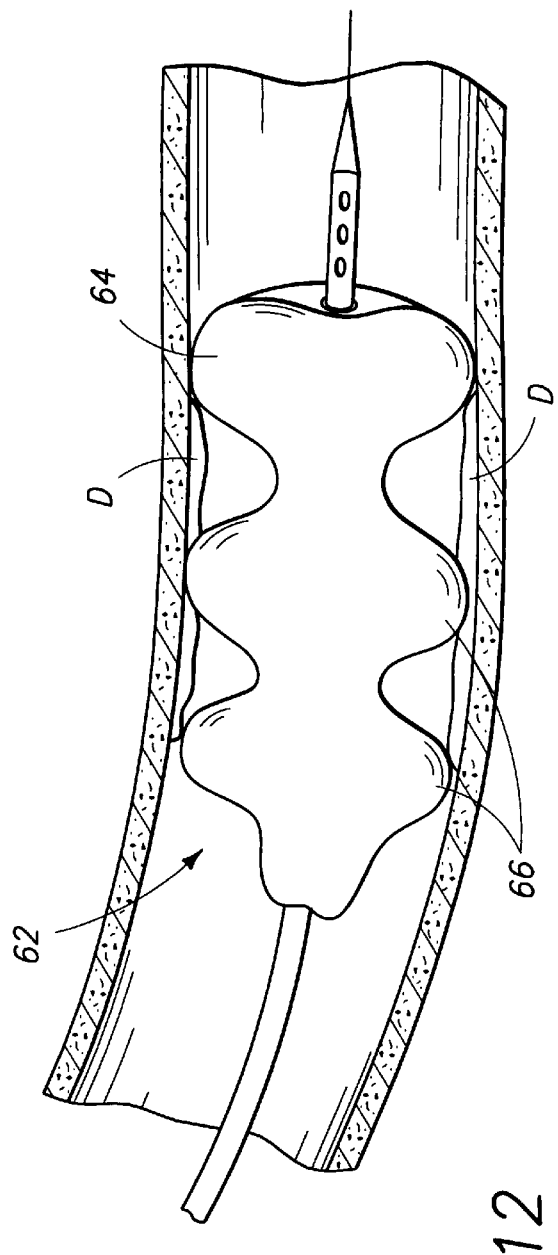
FIG. 11
FIG. 12

EMBOLISM PREVENTION DEVICE

FIELD OF THE INVENTION

The invention relates to embolism-preventing devices, and more particularly, to a device that prevents the free flow of embolism-creating particles that are created during predilation of a vessel or attachment of a stent therein.

BACKGROUND OF THE INVENTION

A stent is a flexible, generally cylindrical object that is typically made of expandable wire mesh. Stents show great promise in opening blocked fluid vessels in the body and in maintaining those vessels in an open state to allow free fluid flow therethrough. Stents have been designed for blood vessels, the urinary tract, the trachea, and other fluid systems in the body.

A stent may be used to open a vein or artery that is blocked by fatty or calcified deposits or other obstructions. A typical method of using such a stent includes inserting a guide wire into the artery and sliding a catheter along the guide wire to the area affected by the deposits. The catheter carries a non-expanded stent thereon, and the stent is positioned adjacent the deposits. The catheter includes a system for expanding the stent, and this is typically done by providing a balloon that is disposed underneath the stent and connected to a passage or lumen within the catheter. When the stent is properly positioned, a burst of air or fluid through the catheter expands the balloon, which in turn permanently expands the stent until the stent contacts the interior wall of the vessel and has a diameter that is substantially the same as the artery. In this manner, the stent traps the fatty deposits against the interior wall of the vein. The catheter is removed from the artery, but the stent remains in the artery to maintain the artery in an open state so that blood may flow freely therethrough.

Although the stent is intended to trap deposits against the interior wall of a vessel, a portion of the deposits may become dislodged from the wall along the ends of the stent as the stent is being placed against the wall. Each dislodged deposit, or embolus, is carried along by the blood flow until it becomes lodged or trapped in a smaller vessel to create an embolism. Since embolisms reduce or cut off blood flow, damage to the body may result, such as tissue damage, heart attack, stroke, or even death.

Researchers have developed devices to eliminate embolus formation during stent attachment. However, these devices are typically bulky and separate from the stent-carrying catheter, and are therefore difficult to insert into the vessel while the catheter is also present in the artery. Furthermore, the balloon that expands the stent cuts off blood flow in the vessel when it is expanded. Because of the difficulty of simultaneously inserting a catheter and a separate embolism prevention device, the blood flow may be constricted or occluded for as long as ten minutes. This causes a deficiency of blood to parts of the body due to the obstruction of the artery. This condition is known as ischemia, and may result in tissue damage.

Emboli may also be created by balloons that are used in predilation systems. The balloon is attached to a catheter, which is positioned in an artery, and the balloon is expanded to dilate the vessel. Emboli created by predilation systems pose serious health risks, as described above, yet known predilation systems do not adequately prevent or remove emboli from the bloodstream.

SUMMARY OF THE INVENTION

The invention is a stent delivery system for use in a fluid conduit in a body. The system includes a catheter that is configured to be placed into a designated region of the conduit. A stent is configured to be moved into the designated region of the conduit by the catheter and placed upon an interior wall of the conduit. A conduit blockage mechanism is mounted on the catheter distal from the stent and is configured to block the conduit while the stent is being placed upon the interior wall.

Another aspect of the invention provides a predilation system for use in a fluid conduit in a body such conduit includes but are not limited to the carotid arteries, renal arteries, peripheral arteries, saphenous vein grafts and the coronary arteries. The system includes a catheter that is configured to be placed into a designated region of the conduit, a conduit dilation mechanism that is configured to be moved into the designated region of the conduit by the catheter to selectively contact an interior wall of the fluid conduit, and a conduit blockage mechanism that is mounted on the catheter distal from the conduit dilation mechanism. The conduit blockage mechanism is configured to block the conduit while the conduit dilation system is contacting the interior wall.

The invention also provides a method of preventing emboli from being created during a stent installation process. According to the method, a catheter is inserted into a bodily fluid conduit. The catheter has a stent and a conduit blocking mechanism mounted thereon at separate positions along the catheter. The conduit blocking mechanism is actuated, and the stent is installed onto an interior wall of the conduit. Embolism-forming particles created during the installing process are removed from the conduit. The conduit blocking mechanism is de-actuated, and the catheter is then removed from the conduit.

BRIEF DESCRIPTION OF THE DRAWINGS

FIG. 1 is a side elevational view of a stent delivery system according to an embodiment of the invention.

FIG. 2 is a sectional view of the catheter shown in FIG. 1, the sectional view being taken along lines 2—2 of FIG. 1.

FIG. 5 is a side elevational view of the stent delivery system of FIG. 1, showing a third step in the stent delivery.

FIG. 6 is a side elevational view of the stent delivery system of FIG. 1, showing a fourth step in the stent delivery.

FIG. 11 is a side elevational view of a flexible membrane that may be used with a stent delivery system.

FIG. 12 is a side elevational view of another flexible membrane that may be used with a stent delivery system.

Figure 3:
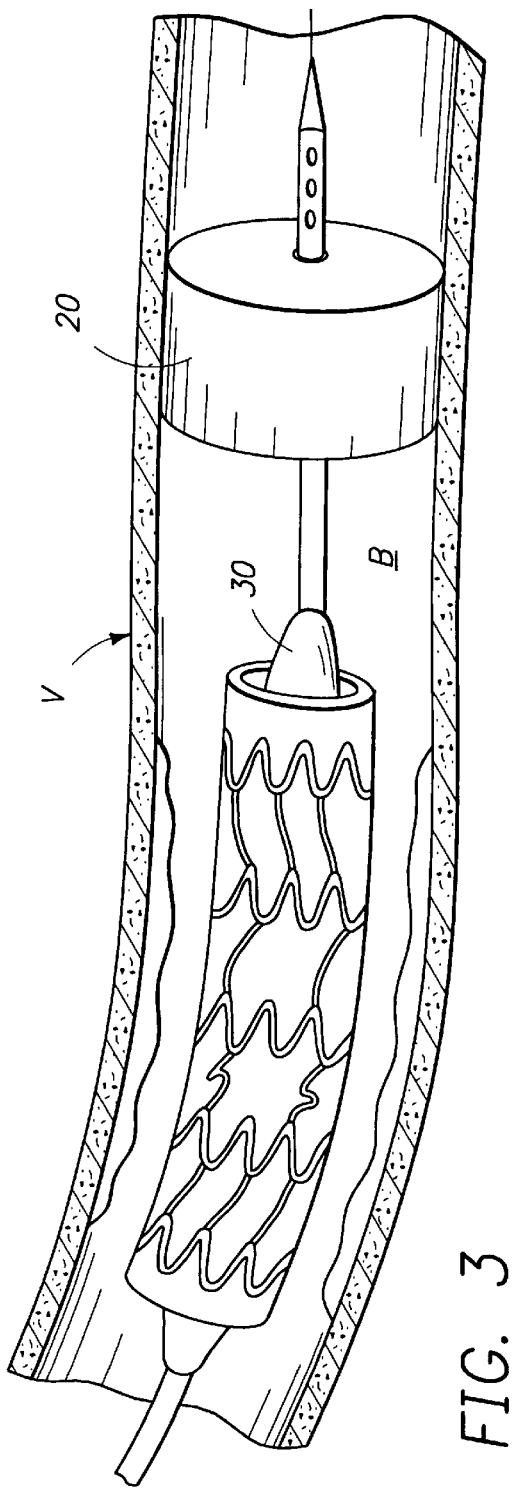
FIG. 3 is a side elevational view of the stent delivery system of FIG. 1, showing a step in the stent delivery.

DETAILED DESCRIPTION OF THE DRAWINGS AND BEST MODE FOR CARRYING OUT THE INVENTION

An embodiment of the invention is depicted in FIGS. 1 and 2, in which a stent delivery system is indicated generally by reference number 10. System 10 includes a transporting mechanism, such as catheter 12, that is movable within a vessel V. The vessel may be a vein, artery, tracheal channel, or may form part of the urinary, renal, or other fluid-transporting systems within a body. However, the embodiment shown in the figures relates specifically to a vein or artery having blood B flowing therethrough. Catheter 12 has a tapered distal end 14. A guide wire aperture 16 is provided at distal end 14 to permit the catheter to be threaded upon a guide wire G as is known in the art. For clarity, guide wire G is not shown in the interior of catheter 12 in FIG. 2.

A conduit blocking mechanism, shown in the figures as a first flexible membrane 20, is disposed upon catheter 12 proximal distal end 14. First flexible membrane 20 encloses a first space 22 that increases and decreases in volume as the first flexible membrane is inflated and deflated. In a preferred embodiment, first flexible membrane 20 is a very compliant, non-tissue-traumatic balloon that expands to a diameter of about 3–10 mm when fully inflated. A first lumen or channel 24 is provided within catheter 12 that communicates, through first apertures 26, with first space 22. A first controlling fluid, such as a saline mixed with I.V. contrast, passes through first channel 24, through first apertures 26, and into first space 28 to inflate and deflate the first flexible membrane.

An instrument, such as second flexible membrane 30, is attached to catheter 12 at a distance d from first flexible membrane. Second flexible membrane 30 encloses a second space 32 that increases and decreases in volume as the first flexible membrane is inflated and deflated. Second flexible membrane 30 may comprise a very compliant, non-tissue-traumatic balloon that expands to a diameter of about 3–10 mm when fully inflated. A second lumen or channel 34 is provided within catheter 12 that communicates, through second apertures 36, with second space 32. A second controlling fluid, such as a saline with contrast, passes through second channel 34, through second apertures 36, and into second space 32 to inflate the second flexible membrane.

Second flexible membrane 30 has first and second ends 30a, 30b and an intermediate portion 30c disposed between the first and second ends.

A stent 40 is mounted in a compressed state upon second flexible membrane 30. As depicted, stent 40 is a non-self-expanding wire mesh cylinder that is configured to contact an interior wall W of vessel V when expanded. Stent 40 has a covering 24 made of a flexible material such as polytetraflouroethylene (PTFE). As will be further described, other types of stents may also be used with the invention.

Figure 4:
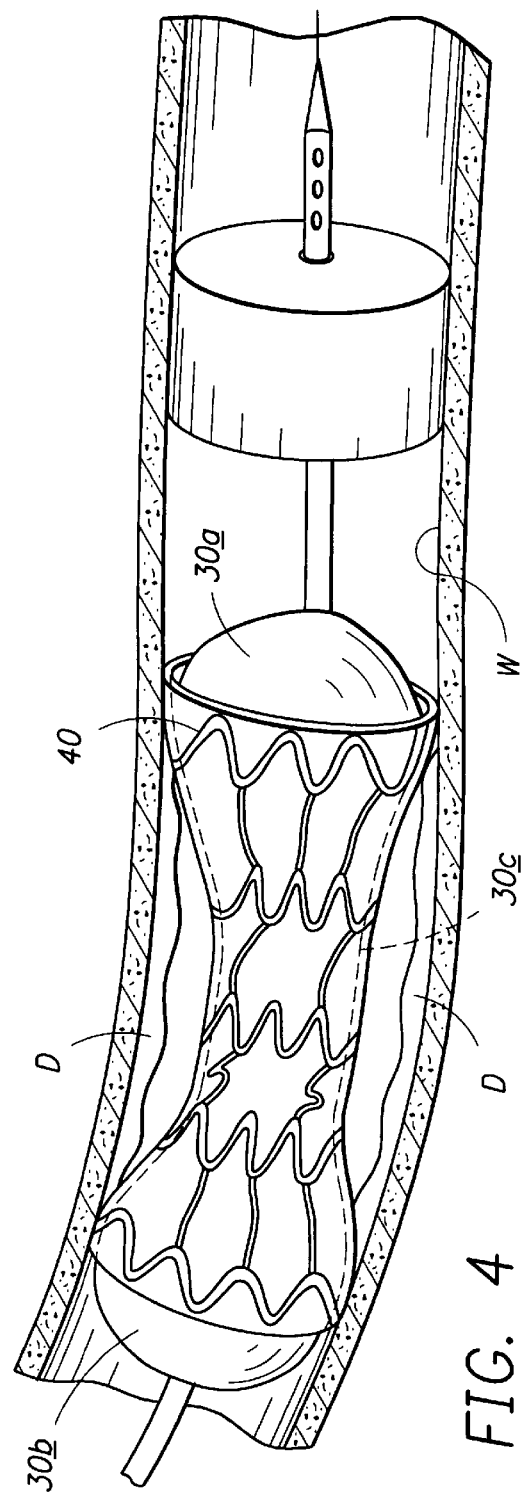
FIG. 4 is a side elevational view of the stent delivery system of FIG. 1, showing a second step in the stent delivery.

FIGS. 1 and 3–7 depict a method of using system 10 to insert stent 40 upon interior wall W. Guide wire G is inserted into vessel V according to known methods. A user directs catheter 12 into the vessel by sliding the catheter upon guide wire G so that stent 40 is positioned within a desired region R of the vessel, as depicted in FIG. 1. With respect to this embodiment, desired region R corresponds to a portion of the vessel having deposits D attached to interior wall W. Deposits D may be made of fatty or calcified material, or may comprise other material that at least partially obstructs the flow of blood B through the vessel. As shown in FIG. 3, the user inflates first flexible membrane 20. When fully inflated, first flexible membrane 20 substantially completely dams or blocks vessel V so that blood B cannot flow through the vessel. The user then inflates second flexible membrane 30. As shown in FIG. 4, second flexible membrane 30 may be designed so that first and second ends 30a and 30b are fully inflated prior to intermediate portion 30c being fully inflated. This inflating strategy is useful to entrap deposits D against the expanding stent, and prevents the deposits from being pushed or "kneaded" out from under the second flexible membrane. As second flexible membrane 30 expands during inflation, stent 40 also expands from its compressed state until it rests against interior wall W and deposits D to trap the deposits between the stent and the interior wall. When the second flexible membrane is fully inflated as shown in FIG. 5, stent 40 has undergone plastic deformation so that it is fully and permanently expanded against interior wall W. Second flexible membrane 30 is then deflated (FIG. 6), and stent 40 remains in contact with the interior wall.

Figure 7:
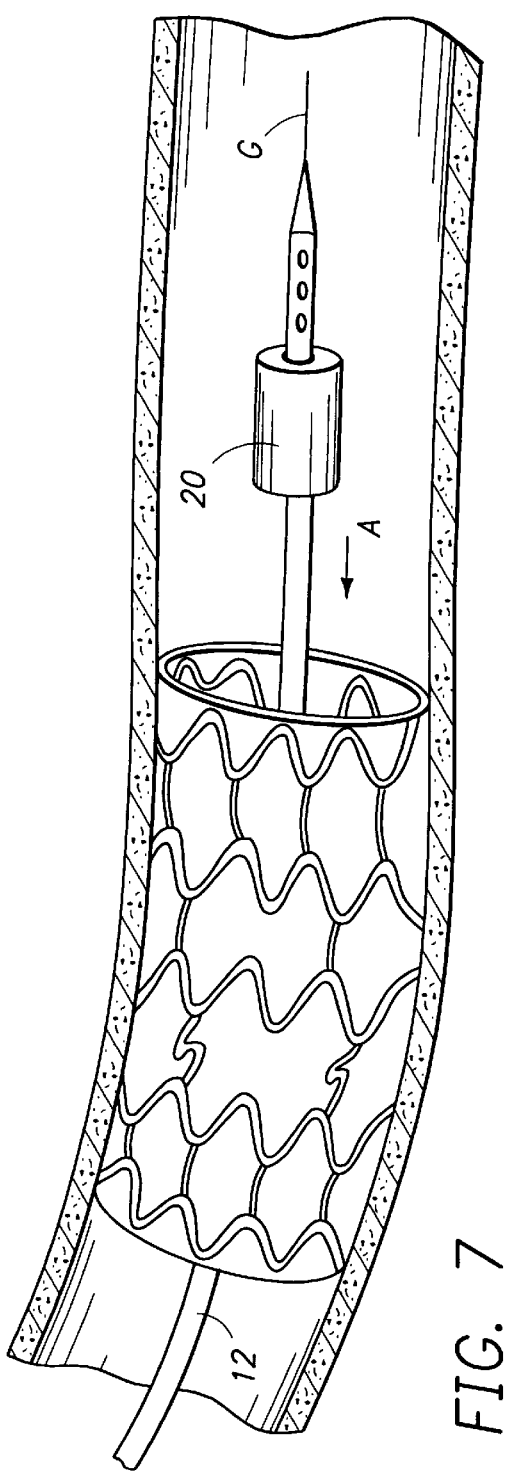
FIG. 7 is a side elevational view of the stent delivery system of FIG. 1, showing a fifth step in the stent delivery.

During the above process, portions of the deposits, which are shown as emboli P, may become dislodged from interior wall W. Emboli P may be of a size to cause an embolism if allowed to freely flow in the blood stream. The particles are removed by inserting a syringe 44 along a guiding catheter (not shown) into the vessel proximal second flexible membrane 30 and drawing blood B and emboli P into the syringe using known suction principles (FIG. 6). Syringe 44 may be a standard luer-lock syringe having a minimum capacity of 30 cc. First flexible membrane 20 is then deflated, as depicted in FIG. 7, to permit normal blood flow through the vessel. Catheter 12 is moved along guide wire G in the direction of arrow A to remove the catheter from the vessel. The guide wire is then removed according to known methods.

The steps in the stent installation method described above may be quickly and efficiently performed so that no embolism-forming particles are left in the blood after the first flexible membrane is deflated. The speed at which the method is performed reduces the time that blood flow is blocked. This in turn reduces the occurrence of ischemia and the resulting tissue damage due to lack of blood flow. Ischemic conditions may be further reduced by incorporating a perfusion apparatus within the catheter, which is depicted as a portion of system 10 in FIGS. 1 and 2. The perfusion apparatus includes a third lumen or channel 46 within the catheter. At least one perfusion inlet aperture 47 is disposed in catheter 12 proximal second end 30b of second flexible membrane. At least one perfusion outlet aperture 48 is disposed at distal end 14 of the catheter. Perfusion fluid F such as blood or other fluid flows into perfusion inlet apertures 47, through third channel 46, through perfusion outlet apertures 48 and into vessel V such that the perfusion fluid bypasses the inflated first and second flexible membranes 20, 30 (FIG. 5). In this manner, blood that has no embolism-forming particles contained therein flows through vessel V without interfering with the stent installation process. Perfusion inlet apertures may include one-way valves or check valves (not shown) to permit the flow of perfusion fluid only from perfusion inlet aperture 47 to perfusion outlet apertures 48. The valves close to prevent perfusion fluid from flowing out of perfusion inlet apertures 47 when syringe 44 is removing emboli from vessel V.

As described above, stent 40 is a non-self-expanding covered stent. A covered stent has been found to decrease restenosis, which is the regrowth of deposits D in region R after the stent has been installed therein. However, in certain circumstances it may be desirable to use an uncovered stent (not shown), which differs from stent 40 in that no covering 42 is provided.

Figure 8:
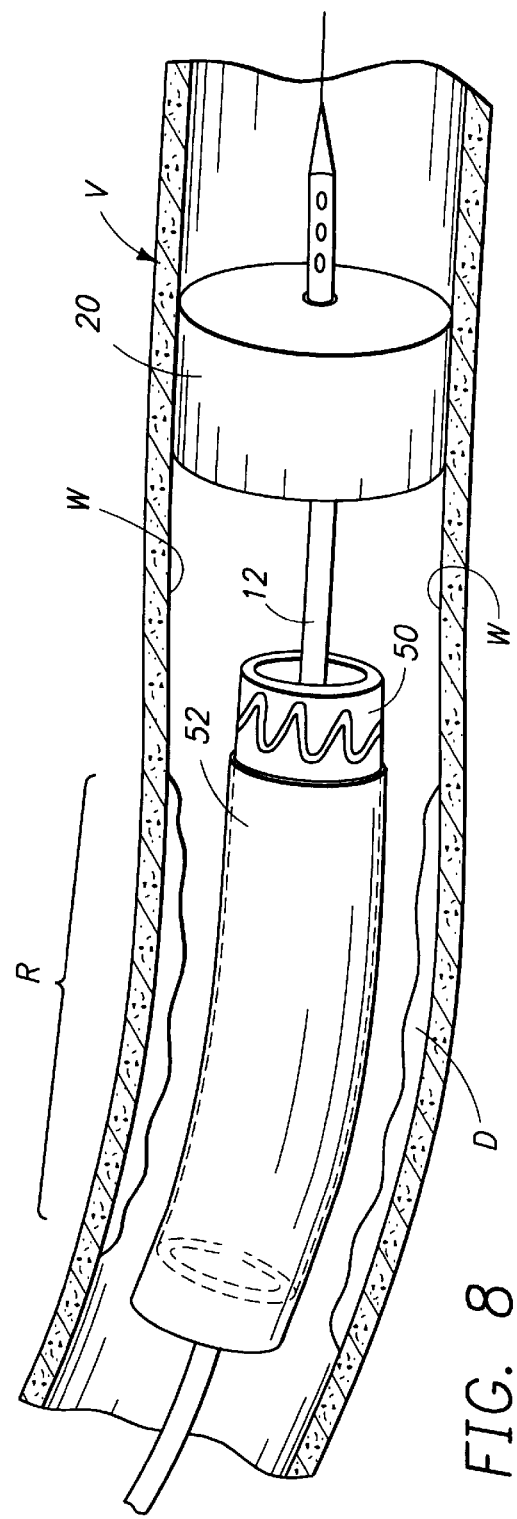
FIG. 8 is a side elevational view of a self-expanding stent delivery system according to the invention.

FIG. 8 depicts another type of stent, known as a self-expanding stent 50, which is usable with system 10. The self-expanding stent is a wire mesh cylinder that is constructed so that in a compressed state the stent is biased to expand to an expanded state. Such a stent does not require the use of a flexible membrane, such as second flexible membrane 30, to expand the stent. A sheath or sleeve 52 surrounds stent 50 while the stent is moved into region R by catheter 12. Once first flexible membrane 20 is inflated, sleeve 52 is removed from around stent 50 using known methods. Stent 50 expands to contact interior wall W of the vessel. Embolism-forming particles are then removed and the first flexible membrane is deflated as described above. Sleeve 52 and catheter 12 are then removed from vessel V using known methods.

Figure 9:
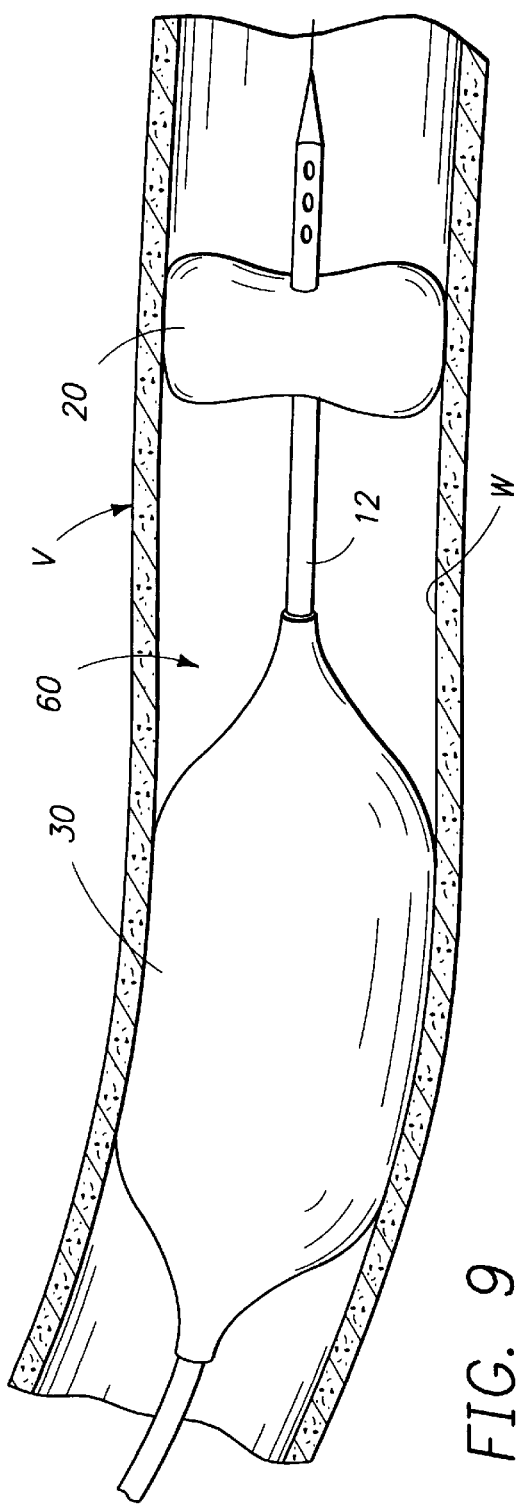
FIG. 9 is a side elevational view of a predilation system according to a second embodiment of the invention.

The invention has been thus far described as being used to install a stent in a vessel. However, the invention is also useful for dilation or predilation, which is the dilation of a vessel prior to performing a surgical or therapeutic technique or operation upon the vessel. FIG. 9 shows a system 60 according to the invention that may be used for predilation. System 60 is similar in construction to system 10 depicted in FIG. 1, and similar components will therefore be identified by similar reference numbers. System 60 includes a catheter 12 and a first flexible membrane 20. A second flexible membrane 30 is attached to catheter 12. In this embodiment, second flexible membrane 30 is configured to be inflated until it contacts interior wall W and dilates vessel V. As with previous embodiments, first and second flexible membranes 20 and 30 are inflatable and deflatable independent of each other. System 60 is used in a manner similar to system 10 of FIGS. 1 and 3–7. Catheter 12 is inserted into vessel V and first flexible membrane 20 is inflated so that fluid flow through the vessel is substantially blocked. Second flexible membrane 30 is inflated to dilate the vessel. When sufficient dilation has been accomplished, the second flexible membrane is deflated and embolism-forming particles are evacuated using a syringe (not shown). First flexible membrane 20 is then deflated, and catheter 12 is removed from vessel V.

Figure 10:
FIG. 10 is side elevational view of a stent delivery system according to third embodiment of the invention.

As previously discussed, second flexible membrane 30 is configured so that first and second ends 30a, 30b are fully inflated prior to the full inflation of intermediate portion 30c. This is done so that deposits D adjacent to intermediate portion 30c are not pushed or "kneaded" toward the first and second ends, where the deposits might break away from interior wall W and form emboli. Because the first and second ends are fully inflated first, such deposits are trapped between the first and second ends. This greatly reduces the formation of emboli. The invention may also use flexible membranes with other inflation strategies, some of which are depicted in FIGS. 10–12. FIG. 10 shows a flexible membrane 62 wherein the end 64 that is proximal distal end of catheter fully inflates prior to the remainder of the flexible membrane being fully inflated. FIGS. 11 and 12 depict another inflation strategy in which intermediate segments 66 of flexible membrane 62 are inflated substantially simultaneously with end 64. Intermediate segments 66 are staggered so that deposits D are trapped between the segments as the segments are fully inflated.

The embodiments described above show that the invention is effective to permit an operation such as predilation or stent installation to be performed on a vessel while ensuring that emboli or other embolism-forming particles created during the operation are removed from the vessel. The invention may also be used with other operations not specifically disclosed herein. The invention may be further varied by using other types of conduit blocking mechanisms, it being understood that the first flexible membranes described above are only exemplary of such blocking mechanisms. The perfusion apparatus may not be included with the embodiments described above, and other ischemia-reducing strategies may be used with the invention. The syringe may have a different capacity. In some circumstances the syringe may be required to have a capacity of 50 cc or more.

Another variation of the invention includes a single flexible membrane that includes a first portion that blocks a conduit when expanded and a second portion that predilates the vessel or installs a stent when expanded. Such an embodiment requires a single lumen and a single controlling fluid that is to be controlled. The selective inflation of the different portions of the flexible membrane may be accomplished by varying the pressure of the controlling fluid or by constructing the portions of the flexible membrane to have different levels of compliance or flexibility.

An advantage of the invention is that the processes of predilation or stent installation takes less time when compared to processes using known embolism-preventing mechanisms. This reduces the occurrence of ischemia and the resultant tissue damage. Ischemic conditions may be further reduced by including a perfusion apparatus, which may be conveniently incorporated into the catheter. Another advantage is that only a single catheter needs to be inserted into the vessel. The invention is less bulky compared to known systems, and may therefore be used in vessels having smaller diameters. Another advantage is that the invention may be used in body conduits other than blood vessels. Still another advantage is that the invention is usable with different types of stents. The invention may also be used with predilation systems or other types of therapeutic or surgical instruments and operations. The invention is therefore useful in a variety of applications.

While the invention has been disclosed in its preferred form, the specific embodiments thereof as disclosed and illustrated herein are not to be considered in a limiting sense as numerous variations are possible. Applicant regards the subject matter of the invention to include all novel and non-obvious combinations and subcombinations of the various elements, features, functions and/or properties disclosed herein. No single feature, function, element or properly of the disclosed embodiments is essential. The following claims define certain combinations and subcombinations which are regarded as novel and non-obvious. Other combinations and subcombinations of features, functions, elements and/or properties may be claimed through amendment of the present claims or presentation of new claims in this or a related application. Such claims are also regarded as included within the subject matter of applicant's invention irrespective of whether they are broader, narrower, or equal in scope to the original claims.

What is claimed is:

1. A stent delivery system for use in a fluid conduit in a body, the conduit having an interior wall, the system comprising:
    a catheter configured to be placed into a designated region of the conduit;
    a pre-formed stent configured to be mounted exterior to the catheter and moved into the designated region of the conduit by the catheter and placed upon the interior wall;
    a conduit blocking mechanism mounted on the catheter distal from the stent and configured to block the conduit while the stent is being placed upon the interior wall;
    wherein, the catheter has a fluid bypass channel that permits fluid to bypass the designated region of the conduit while the conduit blocking mechanism blocks the conduit, and an evacuation apparatus that removes embolism-forming particles from the conduit after the stent is placed upon the interior wall and while the conduit blocking mechanism blocks the conduit.

2. The stent delivery system of claim 1, wherein the stent comprises a wire mesh cylinder.

3. The stent delivery system of claim 1, wherein the stent includes a flexible covering.

4. The stent delivery system of claim 1, further comprising a flexible membrane disposed upon the catheter, wherein the stent is mounted in a compressed state upon the flexible membrane such that inflation of the flexible membrane causes the stent to expand to be placed upon the interior wall.

5. The stent delivery system of claim 4, wherein the flexible membrane has a first end proximal the conduit blocking mechanism, a second end distal from the conduit blocking mechanism, and an intermediate portion between the first and second ends, and wherein the first end of the flexible membrane is constructed with a level of flexibility different from that of the intermediate portion, such that the first end is configured to inflate prior to the inflation of the intermediate portion.

6. The stent delivery system of claim 5, wherein the second end of the flexible membrane is constructed with a level of flexibility different from that of the intermediate portion, such that the second end is configured to inflate prior to the inflation of the intermediate portion.

7. The stent delivery system of claim 5, wherein the first and second ends of the flexible membrane inflate substantially simultaneously.

8. The stent delivery system of claim 1, wherein the stent is nominally encased in a sheath and is self-expanding when the sheath is removed.

9. The stent delivery system of claim 1, wherein the stent is self-expanding.

10. The stent delivery system of claim 1, wherein the catheter has a distal end, and further including an opening disposed at the distal end and communicating with the fluid bypass channel, wherein fluid passes through the fluid bypass channel and the opening to bypass the designated region of the conduit.

11. The stent delivery system of claim 1, wherein the stent includes a covering comprising PTFE.

12. The stent delivery system of claim 1, wherein the evacuation apparatus includes a syringe placed proximal the stent and configured to draw the embolism-forming particles from the conduit.

13. A dilation system for use in a fluid conduit in a body, the conduit having an interior wall, the system comprising:
a catheter configured to be placed into a designated region of the conduit;
a conduit dilation mechanism mounted on the catheter and configured to be moved into the designated region of the conduit by the catheter to selectively contact the interior wall; and
a conduit blocking mechanism mounted on the catheter and configured to block the conduit while the conduit dilation mechanism is contacting the interior wall, wherein the conduit dilation mechanism comprises a flexible membrane, including a first portion and a second portion, wherein the portions are formed with different levels of compliance for selective inflation; and
an evacuation apparatus that removes embolism-forming particles from the conduit after the conduit dilation mechanism contacts the interior wall and while the conduit blocking mechanism blocks the conduit.

14. The dilation system of claim 13, wherein the evacuation apparatus includes a syringe configured to draw the embolism-forming particles from the conduit.

15. The dilation system of claim 13, further comprising a stent configured to be mounted exterior to the catheter and moved into the designated region of the conduit by the catheter and placed upon the interior wall.

16. A dilation system for use in a fluid conduit in a body, the conduit having an interior wall, the system comprising:
a catheter configured to be placed into a designated region of the conduit;
a conduit dilation mechanism mounted on the catheter mid configured to be moved into the designated region of the conduit by the catheter to selectively contact the interior wall; and
a conduit blocking mechanism mounted on the catheter and configured to block the conduit while the conduit dilation system is contacting the interior wall, wherein the conduit dilation mechanism and the conduit blocking mechanism are different portions of a single flexible membrane; and
an evacuation apparatus that removes embolism-forming particles from the conduit after the conduit dilation mechanism contacts the interior wall and while the conduit blocking mechanism blocks the conduit.

* * * * *